(12) United States Patent
Sanchez Gomez

(10) Patent No.: US 6,736,142 B2
(45) Date of Patent: May 18, 2004

(54) PROTECTIVE TUBE AND HARNESS

(76) Inventor: Gines Sanchez Gomez, Calle Cervantes, 1, 7, B, Mostoles (Madrid) 28.932 (ES)

( * ) Notice: Subject to any disclaimer, the term of this patent is extended or adjusted under 35 U.S.C. 154(b) by 122 days.

(21) Appl. No.: 10/185,634

(22) Filed: Jun. 24, 2002

(65) Prior Publication Data

US 2003/0056798 A1 Mar. 27, 2003

(51) Int. Cl.⁷ .............................................. A61B 19/00
(52) U.S. Cl. ...................... 128/869; 128/883; 600/39
(58) Field of Search ................... 128/869, 883; 600/38, 39, 41; 434/262

(56) References Cited

U.S. PATENT DOCUMENTS

| | | | | |
|---|---|---|---|---|
| 104,117 A | * | 6/1870 | Cook | 128/883 |
| 587,994 A | * | 8/1897 | McCormick | 128/883 |
| 875,845 A | * | 1/1908 | Perkins | 128/883 |
| 934,240 A | * | 9/1909 | Tunnessen | 128/883 |
| 995,600 A | * | 6/1911 | Heyser | 128/883 |
| 1,215,028 A | * | 2/1917 | Jones | 128/883 |
| 1,865,280 A | * | 6/1932 | Risley | 128/883 |
| 4,164,217 A | * | 8/1979 | Schrock | 128/883 |
| 5,368,050 A | * | 11/1994 | Donelan | 128/884 |
| 5,485,636 A | * | 1/1996 | Yandell | 2/406 |

* cited by examiner

*Primary Examiner*—Henry Bennett

(57) ABSTRACT

Protective tube and harness for the masculine member. The tube continues with a hinge with a hole at their end. The member is placed into the said tube, fixed with adhesive tape to the hinge. This hinge is introduced in an external tube with another hole which matches with the hinge hole. A padlock fixes the hinge and the external tube. Two rings are added to the external tube in their ends being fixed to the human body with a harness by a cable or chain.

6 Claims, 3 Drawing Sheets

PROTECTIVE TUBE AND HARNESS

TECNICAL FIELD

The invention belongs to entertainment field, essentially of erotic games.

BACKGROUND OF THE INVENTION

The medieval apparatus named chastity belt it is well known as way to control sexual activity of women. To control sexual activity of men many apparatuses have been intended with said function. The patents U.S. Pat. No. 0,104,117, U.S. Pat. No. 0,587,994, U.S. Pat. No. 0,875,845, U.S. Pat. No. 0,934,240, U.S. Pat. No. 0,995,600, U.S. Pat. No. 1,215,028, U.S. Pat. No. 1,865,280, U.S. Pat. No. 4,164,217, U.S. Pat. No. 5,368,050, U.S. Pat. No. 5,485,636 have this function.

The most used apparatuses are next:

chastity cage. It is fixed to testicles base. To be effective it would to be fixed very tight, what can hinder blood circulation chastity bracelet. It is fixed to penis surface for a rough surface or with thorns. Same inconvenience that previous chastity device classic. It is similar feminine belt, but in their shield it has a sujección element that it is a tube which holds the penis and it is fixed inwardly. An almost perfect adjustment is needed to be effective.

BRIEF SUMMARY OF THE INVENTION

The penis is bandaged with adhesive tape that impedes his expansion, and this adhesive tape is covered with a safety element (be. a tube). This safety tube is fixed to the adhesive tape with a hinge through the whole length of penis and this hinge is fixed to the previous bandage, or directly to the penis (so adhesive tape has two functions in this way).

Junction between hinge and safety element it is with a padlock.

The whole thing is a chastity tube.

DETAILED DESCRIPTION OF THE INVENTION

Figure 1:
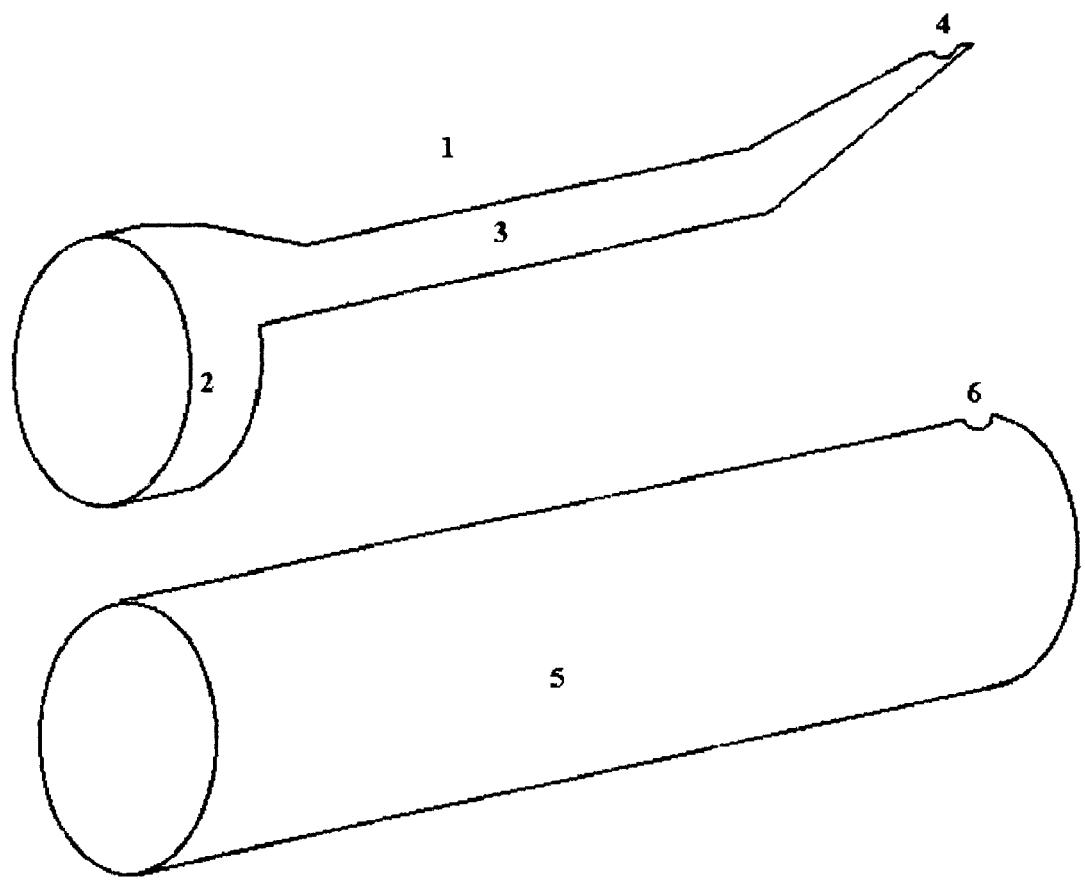
FIG. 1. Fixation piece to penis and safety tube.

Chastity tube has two pieces (padlock and adhesive tape are not included in the invention, but yes the sujección that they cause). Both pieces are represented in FIG. 1.

The first piece (1), to fix the penis, it is a small tube (2) with interior diameter lightly superior to the flabby penis. It holds a hinge (3) through the whole length penis. This hinge is lightly longer that penis. At the end of hinge there is a hole (4) with enough diameter for a padlock.

The second piece is a safety tube which is a normal tube (5) with interior diameter lightly superior to the piece of previous paragraph, with a hole (6) of enough diameter for a padlock located so that matches with the hole hinge.

Both pieces are lined with rubber, well for immersion in rubber paint or for immersion in fused rubber.

Figure 2:
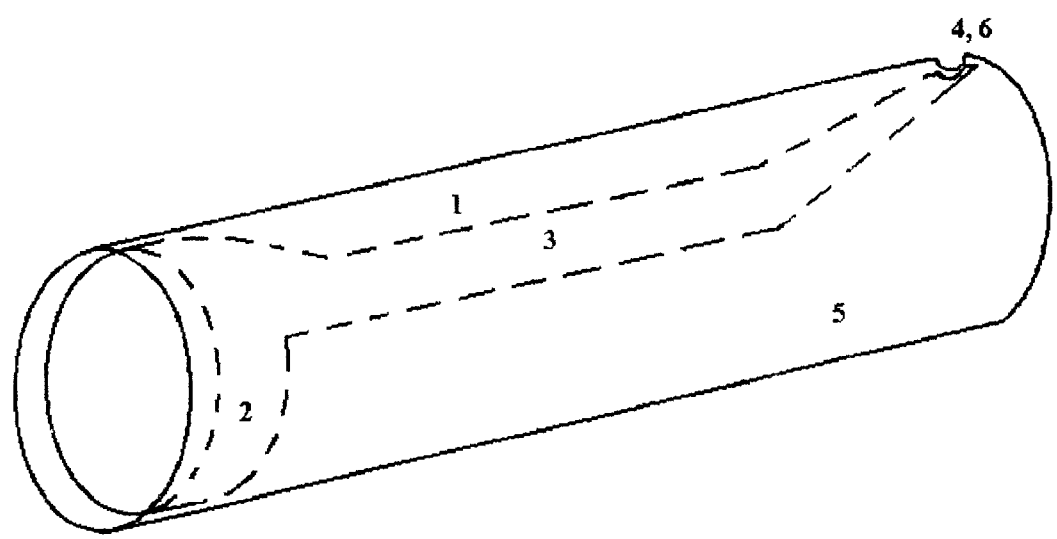
FIG. 2. Whole chastity tube set.

Functioning of apparatus is as following: the fixation piece is introduced (1) in the penis until their bottom. With adhesive tape the penis is fixed to the hinge by bandaging. The safety tube (5) is placed on this set, as it is schematized in FIG. 2. Both pieces are blocked with a padlock in the tip through the holes (4, 6).

Figure 3:
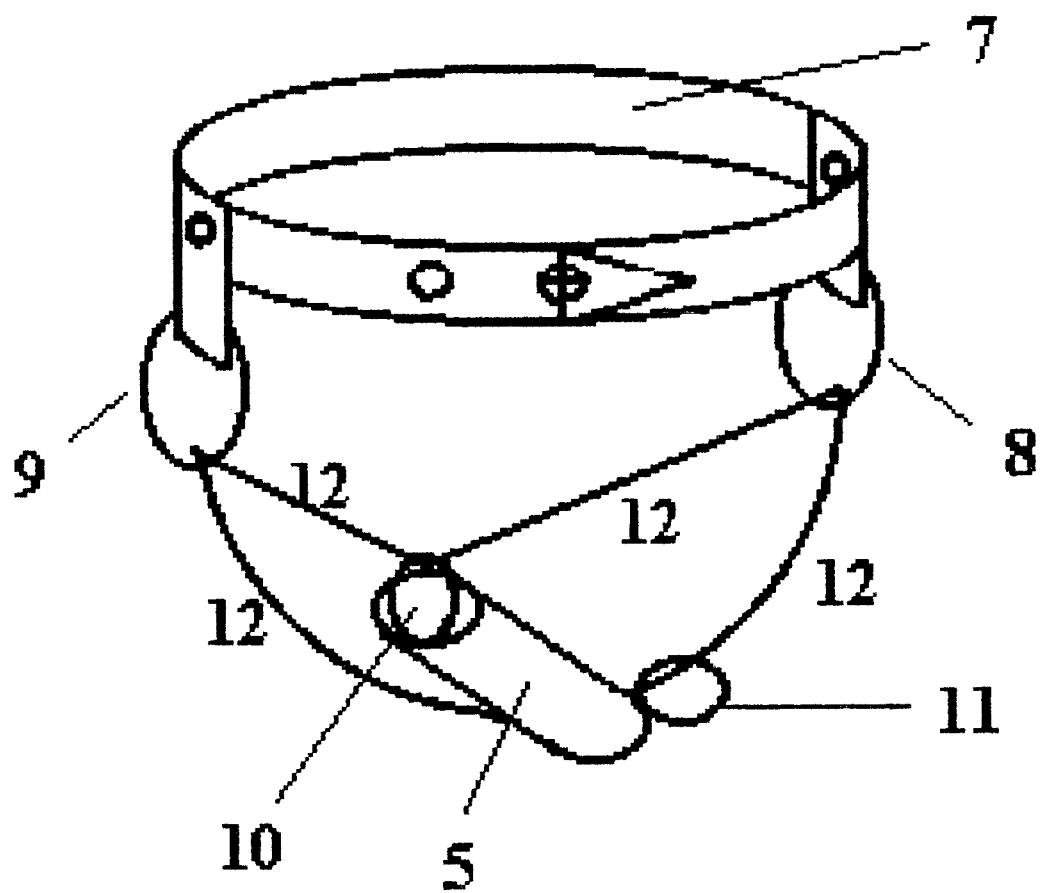
FIG. 3. Chastity tube and fixation harness to the masculine body.

Ending, the chastity tube can be mounted in the masculine body with a harness as it is schematized in FIG. 3. This harness has the purpose of avoiding that the tube chastity can move itself, by fitting to masculine body, and also as an additional element of security. It is a belt (7) with two rings in each lateral (8, 9), while the chastity tube is provided with two rings (10, 11), one in each end. A leather strap, cable or chain (12) links the four rings (8 to 11) following the following way: superior ring of chastity tube (10), right stomach of masculine body, right ring of belt (8), right bottom and right thigh of masculine body, inferior ring of chastity tube (11), left thigh and left bottom of masculine body, left ring of belt (9), left stomach of masculine body, and superior ring of chastity tube (10).

OTHER EMBODIMENTS OF THE INVENTION

A very simple is a strap of material of enough resistance (the leather is very appropriate) with longitude lightly superior to penis with a hole in the tip, with a reinforcement rivet, and a tube of aluminum with diameter lightly superior that the masculine penis. The strap is fixed to penis with adhesive tape in all its longitude. Then it is covered with the aluminum tube that is held by a padlock that go through the hole of the strap and aluminum tube.

In addition leather strap can be riveted, at its testicles end, with a riveted metallic piece with a groove, matching with safety tube.

About the fixation harness to masculine body, it can be secured with padlocks. The fixation harness can be metallic also. Salid fixation harness can be totally adjustable also if belt is itself adjustable, and the ring of belt and chastity tube are linked with a chain. In this case the chain (covered of leather, plastic or rubber) can be adjusted with the padlock of the chastity tube, being eliminated the ring (11) of one of the ends of chastity tube that is substituted by the padlock loop.

INDUSTRIAL APPLICATION

Essentially the inventin is for games of erotic type.

I claim:

1. A method to assure masculine chastity characterized in that the penis is bandaged with an adhesive tape, and the bandage is protected externally by a metallic tube, being the sujección of the bandage to the external tube through a hinge that run through the penis in all his longitude, being fixed the hinge to the penis with the said adhesive tape, and being linked the external tube and the hinge by a padlock.

2. A chastity set to assure masculine chastity characterized by a tube of small longitude and with diameter lightly bigger that penis which is prolonged with a hinge of longitude lightly superior that penis, being perforated near their tip, said tube-hinge is fixed to the penis with an bandage of adhesive tape, being covered the tube-hinge and the bandage with a safety tube of longitude lightly superior that the penis with a hole near their tip, being blocked the safety tube and the tube-hinge by a padlock through the holes of each one of both pieces, being fixed the safety tube to the masculine body with a harness which is a belt with two rings in their lateral, other two rings are fixed at the ends of the safety tube, being linked the four rings with a cable, strap or chain.

3. The chastity set according with claim 2 characterized in that the tube-hinge is of copper and the safety tube is of aluminum.

4. The chastity according with claim 2 characterized in that the small interior tube of the tube-hinge is located half of the tube-hinge.

5. The chastity set according with claim 2 characterized in that the tube-hinge is changed by a strap of enough resistance as leather, copper, etc., being reinforced in both ends with metallic elements, having the nearest reinforcement piece to the testicles a groove to adjust to the safety tube.

6. The chastity set according with claim 2 characterized in that the fixation harness has also a safety function, being metallic and adjustable, and with a chain that runs through the two rings of belt and by the superior ring of chastity tube, being changed the inferior ring of chastity tube by the padlock, assuring said padlock both the chastity tube and the chain.

\* \* \* \* \*